(12) United States Patent
Kiersey et al.

(10) Patent No.: US 12,383,193 B2
(45) Date of Patent: Aug. 12, 2025

(54) SKIN INSPECTION DEVICE FOR IDENTIFYING ABNORMALITIES

(71) Applicant: BLUEDROP MEDICAL LIMITED, Galway (IE)

(72) Inventors: Simon Kiersey, Galway (IE); Gavin Corley, Ennis (IE); Christopher Murphy, Dublin (IE)

(73) Assignee: BLUEDROP MEDICAL LIMITED, Galway (IE)

( * ) Notice: Subject to any disclaimer, the term of this patent is extended or adjusted under 35 U.S.C. 154(b) by 0 days.

(21) Appl. No.: 18/344,851

(22) Filed: Jun. 29, 2023

(65) Prior Publication Data

US 2024/0000374 A1    Jan. 4, 2024

(30) Foreign Application Priority Data

Jun. 30, 2022 (GB) .................................... 2209656

(51) Int. Cl.
*A61B 5/01* (2006.01)
*A61B 5/00* (2006.01)
*G03B 37/06* (2021.01)

(52) U.S. Cl.
CPC ............ *A61B 5/447* (2013.01); *A61B 5/0077* (2013.01); *A61B 5/445* (2013.01);
(Continued)

(58) Field of Classification Search
None
See application file for complete search history.

(56) References Cited

U.S. PATENT DOCUMENTS

2005/0171456 A1* 8/2005 Hirschman .......... A61B 5/1036
600/592
2009/0186759 A1* 7/2009 Lin ..................... B41M 7/0027
503/215

(Continued)

FOREIGN PATENT DOCUMENTS

EP          3179902 B1     10/2020
GB          2550582 A      11/2017
WO       2021185782 A1     9/2021

OTHER PUBLICATIONS

Extended European Search Report, EP23181246.2, Nov. 29, 2023, 6 pages.
Search Report, GB2209656.4, Dec. 12, 2022, 1 page.

*Primary Examiner* — Tse W Chen
*Assistant Examiner* — Martin Nathan Ortega

(57) ABSTRACT

A skin inspection device for identifying abnormalities is described. The device comprises a transparent panel having an inspection area; an array of thermochromic liquid crystal (TLC) formations provided on the transparent panel which are operable to change colour in response to a change of temperature; one or more image capture devices having a wide angle lens for capturing an image of the TLC formations and an area of skin of a target located in the inspection area; at least some of the TLC formations have a warped shape while other TLC formations have a non-warped shape; wherein the warped shaped TLC formations and the non-warped TLC formations define a pattern such that when viewed through the wide angle lens both the warped shaped TLC formations and the non-warped TLC formations appear non-warped.

22 Claims, 11 Drawing Sheets

(52) U.S. Cl.
 CPC ............... *A61B 2560/0223* (2013.01); *A61B 2562/0261* (2013.01); *A61B 2562/0276* (2013.01); *A61B 2562/046* (2013.01); *A61B 2562/185* (2013.01); *A61B 2576/02* (2013.01)

(56) References Cited

U.S. PATENT DOCUMENTS

| | | | |
|---|---|---|---|
| 2011/0077527 A1* | 3/2011 | Yang | A61B 5/489 |
| | | | 428/32.6 |
| 2012/0249727 A1* | 10/2012 | Corcoran | G06T 3/12 |
| | | | 348/E5.078 |
| 2014/0121479 A1* | 5/2014 | O'Connor | A61B 5/447 |
| | | | 600/407 |
| 2014/0121532 A1 | 5/2014 | O'Connor et al. | |
| 2017/0224257 A1* | 8/2017 | Rogers | A61B 5/0537 |
| 2018/0014734 A1* | 1/2018 | Rogers | A61B 5/0205 |
| 2019/0200917 A1* | 7/2019 | Murphy | A61B 5/0077 |
| 2019/0209076 A1 | 7/2019 | Murphy et al. | |
| 2021/0069390 A1* | 3/2021 | Gross | A61P 17/16 |
| 2023/0377198 A1* | 11/2023 | Lee | G06T 7/60 |

\* cited by examiner

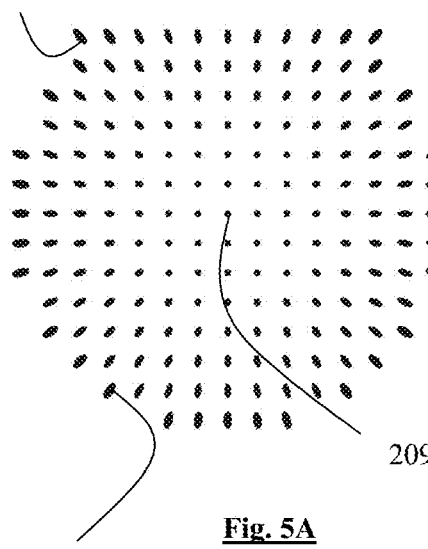
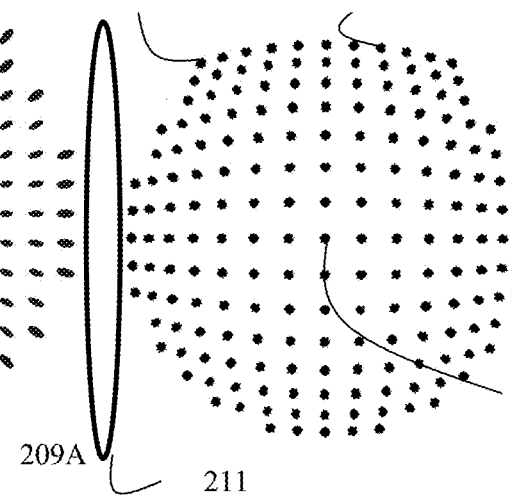
Fig. 5A          Fig. 5B
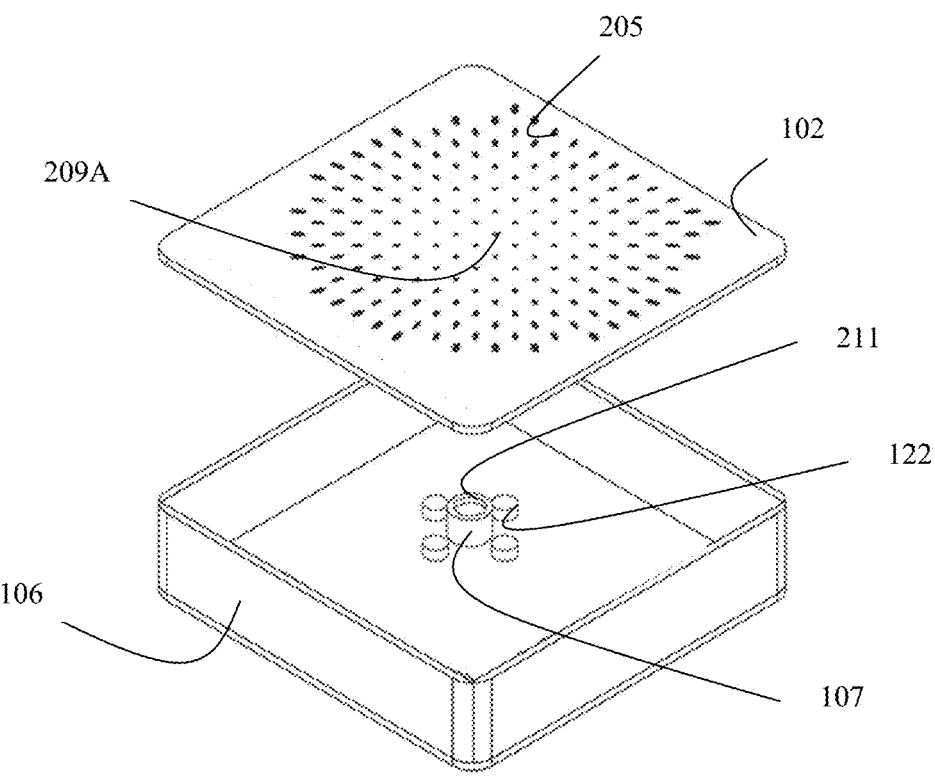
Fig. 5C

SKIN INSPECTION DEVICE FOR IDENTIFYING ABNORMALITIES

FIELD OF THE INVENTION

The present disclosure relates to a skin inspection device for identifying abnormalities. In particular, but not exclusively, the skin inspection device relates to heat sensing a sole of a human foot in order to predict the formation of ulcers.

BACKGROUND

Diabetics commonly suffer from a condition known as diabetic foot ulcers (DFU) over their lifetime. It is recommended that diabetics inspect their feet daily so as detect any abnormal damage to the skin that may be an indicator of the onset of DFU. However, limiting factors such as reduced vision, reduced mobility, lack of sensation due to peripheral neuropathy, and a lack of education results in diabetics failing to adhere to daily foot inspections as recommended. Early identification of DFUs may result in improved outcomes and reduced medical treatment costs. If DFUs are detected before they form the benefit would be even greater. Currently the best practice is to visually inspect the feet and report to a podiatrist periodically.

Temperature monitoring is a known method of predicting DFU formation. A temperature difference of 2.2° C. between similar points on opposite feet has been shown to indicate inflammation which may be a precursor to ulceration. Temperature point probes are known in the art which allow patients to take temperatures on the bottom of both feet so that temperature comparisons may be made from spot to spot. Such point probes may be used to measure skin temperature at individual target spots. If a spot on one foot demonstrates a change in temperature, compared to the same spot on the other foot, and sustains that change in temperature or higher (rises to four degrees Fahrenheit (2.2° C.) or more for two days or more) it indicates that a problem may be occurring and the patient is alerted to consult their doctor. The difficulty with this approach is that the same spot of the patients foot requires to be measured over a number of days. It is difficult for a patient to identify the same spot in order to accurately take measurements. Furthermore, the onus is on the patient to maintain a log of the temperature readings in order to do the comparisons which may result in human error. Daily visual inspection of the feet is recommended for all diabetics. As mentioned, this can be difficult due to poor vision and mobility. Current temperature monitoring devices do not facilitate the recommended daily visual inspection.

Published PCT Patent Application no. WO2017202534 of the present Applicant utilises thermochromic liquid crystal (TLC) which change colour with respect to temperature. Temperature is measured using a light source, lens, and image sensor to record regions of TLC. The captured image is then be analysed to measure the colour of the TLC at a Region of Interest (ROI). The temperature may then be determined by using a calibration equation and the measured colour to calculate temperature. The array of TLC sensors are designed such that optical pathways exist between sensors, thus allowing visualisation of the target behind the sensors while recording the image of the TLC sensors. Such a design is useful for the detection of abnormalities which may present either or both thermal and visual signals. The pattern of TLCs 100 which are illustrated in FIG. 1 define a uniform pattern where the TLCs are substantially the same shape and dimensions. One of the drawbacks of a uniform pattern of TLCs is that if the image capture device has a wide angle lens the captured image is distorted which results in a change in the geometry of TLC in the image. By way of example, a rectilinear checker board as illustrated in FIG. 2a when viewed through a wide angle lens will be distorted as shown in the FIG. 2B, where the level of distortion and reduction in size of each square increases with distance from the centre of the image.

There is a need for a skin inspection device which addresses at least some of the drawbacks of the prior art.

SUMMARY

These and other problems are addressed by providing a skin inspection device for identifying abnormalities; the device comprising:
  a transparent panel having an inspection area;
  an array of thermochromic liquid crystal (TLC) formations provided on the transparent panel which are operable to change colour in response to a change of temperature;
  one or more image capture devices having a wide angle lens for capturing an image of the TLC formations and an area of skin of a target located in the inspection area;
  at least some of the TLC formations have a warped shape while other TLC formations have a non-warped shape;
  wherein the warped shaped TLC formations and the non-warped TLC formations define a pattern such that when viewed through the wide angle lens both the the warped shaped TLC formations and the non-warped TLC formations appear non-warped.

In one embodiment, the amount of warping of the warped shaped TLC formations increases towards the periphery of the pattern.

In another embodiment, the shape of the TLC formations vary in size relative to a centre of the pattern such that the TLC formations towards the periphery of the pattern are larger than the TLC formations adjacent the centre of the pattern.

In a further embodiment; the warp angle of the warped TLC formations vary such that the TLC formations towards the periphery of the pattern have a larger warp angle than the TLC formations adjacent the centre of the pattern.

In an exemplary embodiment; the captured image of the TLC formations have uniform dimensions irrespective of their position in the pattern. Advantageously, the captured image of the TLC formations have a uniform shape irrespective of their position in the pattern. Preferably, the captured image of the TLC formations have a uniform angle irrespective of their position in the pattern. In a exemplary embodiment, the captured image of the TLC formations have uniform dimensions irrespective of their position in the pattern.

In one embodiment; the geometry of the TLC formations are tuned to the parameters of a particular wide angle lens. Advantageously, the parameters may include at least one of focal length and field of view.

In an exemplary embodiment; the geometry of the TLC formations are tuned to the parameters of a particular image sensor. Advantageously, the parameters of the image sensor include at least one of resolution and aspect ratio.

In another embodiment; the TLC formations extend radially from a centre point in the pattern and the level of warping of the TLC formations increases the further the TLC formation is located from the centre point. Advantageously, the warp angle of the warped TLC formations increases the further the TLC formations is located from the centre point. Preferably, the size of the warped TLC formations increases the further the TLC formations is located from the centre point.

The present disclosure also relates to a method for identifying skin abnormalities; the device comprising:
  providing a transparent panel having an inspection area;
  providing an array of thermochromic liquid crystal (TLC) formations on the transparent panel which are operable to change colour in response to a change of temperature;
  providing one or more image capture devices having a wide angle lens for capturing an image of the TLC formations and an area of skin of a target located in the inspection area; at least some of the TLC formations have a warped shape while other TLC formations have a non-warped shape;
  wherein the warped shaped TLC formations and the non-warped TLC formations define a pattern such that when viewed through the wide angle lens both the the warped shaped TLC formations and the non-warped TLC formations appear non-warped.

These and other formations will be better understood with reference to the followings Figures which are provided to assist in an understanding of the present teaching.

BRIEF DESCRIPTION OF THE DRAWINGS

The present teaching will now be described with reference to the accompanying drawings in which:

FIGS. 5A and 5B illustrates a skin inspection device in accordance with the present teaching

DETAILED DESCRIPTION OF THE DRAWINGS

Figure 1:
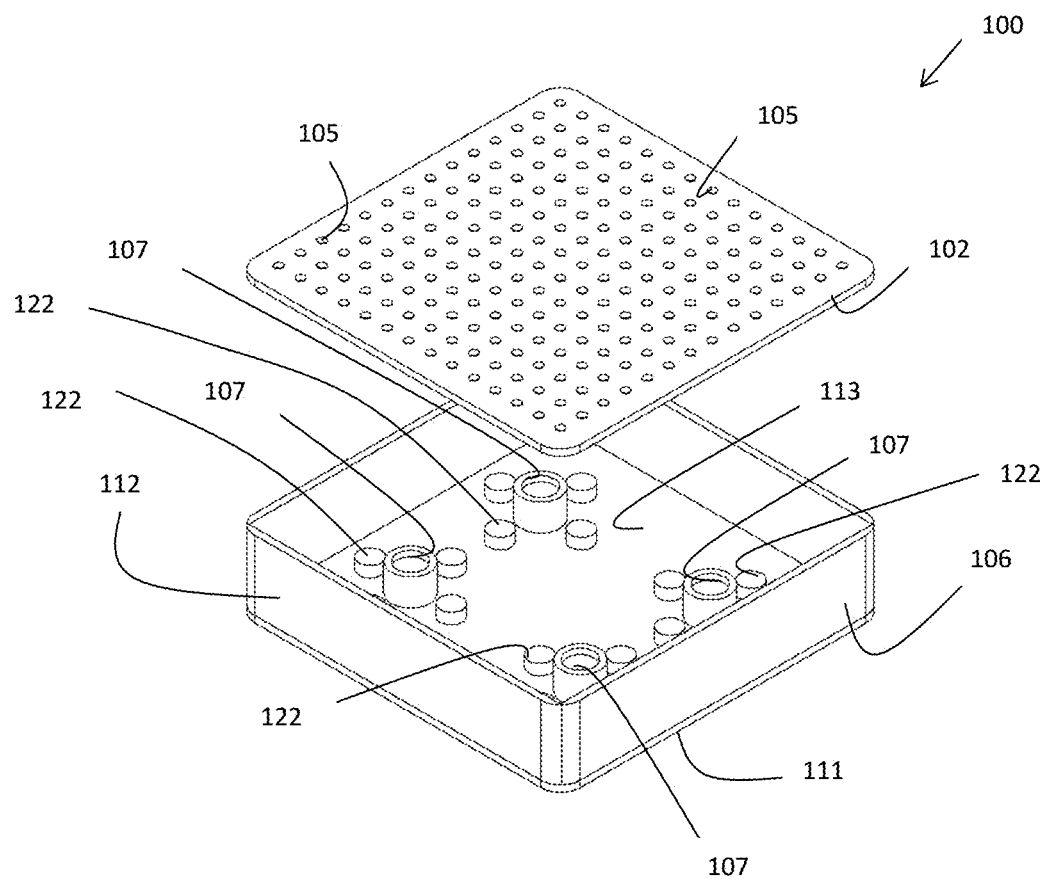
FIG. 1 illustrates a prior art skin inspection device.

The present disclosure will now be described with reference to some exemplary skin inspection devices. It will be understood that the exemplary skin inspection devices are provided to assist in an understanding of the teaching and is not to be construed as limiting in any fashion. Furthermore, elements or components that are described with reference to any one Figure may be interchanged with those of other Figures or other equivalent elements without departing from the spirit of the present teaching. It will be appreciated that for simplicity and clarity of illustration, where considered appropriate, reference numerals may be repeated among the figures to indicate corresponding or analogous elements.

Referring to the drawings and initially to FIG. 1 which discloses the prior art skin inspection device 100 of Published PCT Patent Application no. WO2017202534. The device 100 comprises a transparent panel 102 which defines an inspection area for co-operating with a region of a body under inspection. For example, the region under inspection may be a foot, a hand, an arm, a leg, etc. In the exemplary arrangement, the region under inspection is a sole of a foot 109 as illustrated in FIG. 2. The transparent panel 102 provides a foot plate which accommodates the foot 109 during inspection. An array of thermochromic liquid crystal (TLC) formations 105 are provided on the transparent panel 102 which are operable to change colour in response to detecting a change of temperature.

The transparent panel 102 is supported on a housing 106 which accommodates the components of the device 100 therein. The housing 106 comprises a base 111 with side walls 112 extending upwardly therefrom which together define a hollow interior region 113. One or more image capture device 107 are provided in the hollow interior region 113 for capturing a colour image of the TLC formations and an area of skin located on the foot 109. One or more light sources in the form of LEDs 122 may also be located within the hollow interior region 113. Other types of light sources other that LEDS may be used such as cold cathode lamps, electroluminescent coated materials, for example, tapes, panels, wires, xenon or halogen bulbs. A central processing unit 115 is also provided within the hollow interior region 113 and is configured to control the operations of the device 100 as described in detail below.

Thermochromism is the property of a substance to change colour due to a change in temperature as is well known in the art. The TLC dots 105 are engineered to change colour at precise temperatures and are used as a way of determining foot temperature. The TLC dots 105 change colour over a predefined range, for example from red to blue over the course of a temperature range of 20° C., for example, with red being 20° C. and blue being 40° C. The temperature range required for the application of diabetic foot ulcers is 15-38° C. The TLC dots 105 change colour in response to heat. A digital photographic image of the TLC dots 105 is taken by the image capture device 107. A CPU 115 is configured to analyse the image of the TLC dots 105. The CPU 115 is operable to analyse for colour change and convert the colour information into temperature values. Thus the colour of the TLC dots 105 indicates the temperature at various points on the foot that are in registration with the TLC dots. If a point on one foot demonstrates a change in temperature, compared to the same point on the other foot, and sustains that change in temperature or higher (rises to four degrees Fahrenheit (2.2° C.) or more for two days or more) the CPU 115 may be configured to indicate that a DFU problem may be occurring and the patient is alerted to consult their doctor.

Figures 4A, 4B:
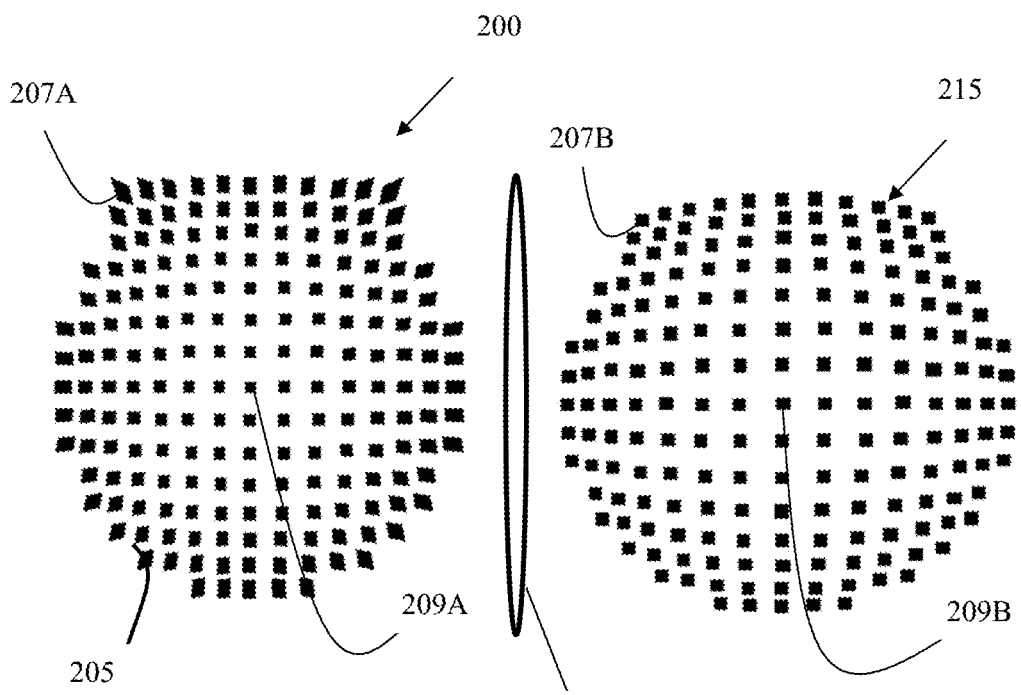
FIGS. 4A, 4B and 4C illustrates a skin inspection device in accordance with the present teaching.

Referring now to FIG. 4A which illustrates a skin inspection device 200 in accordance with the present invention. The skin inspection device 200 is substantially similar to the skin inspection device 100 and like elements are indicated by similar reference numerals. The main difference between the skin inspection device 200 and skin inspection device 100 is that in the device 200 the pattern of TLC formations 205 on the transparent panel have been arranged to eliminate image distortion when the image capture device has a wide angle lens. The skin inspection device 200 comprises transparent panel 105 having an inspection are. An array of thermochromic liquid crystal (TLC) formations 205 are provided on the transparent panel which are operable to change colour in response to a change of temperature. One or more image capture devices 107 having a wide angle lens are provided for capturing an image of the TLC formations 205 and an area of skin of a target located in the inspection area. The pattern of the TLC formations 205 are arranged such that at least some of the TLC formations have a warped shape 207A, 207B while other TLC formations have a non-warped shape 209A, 209B.

Figure 4C:
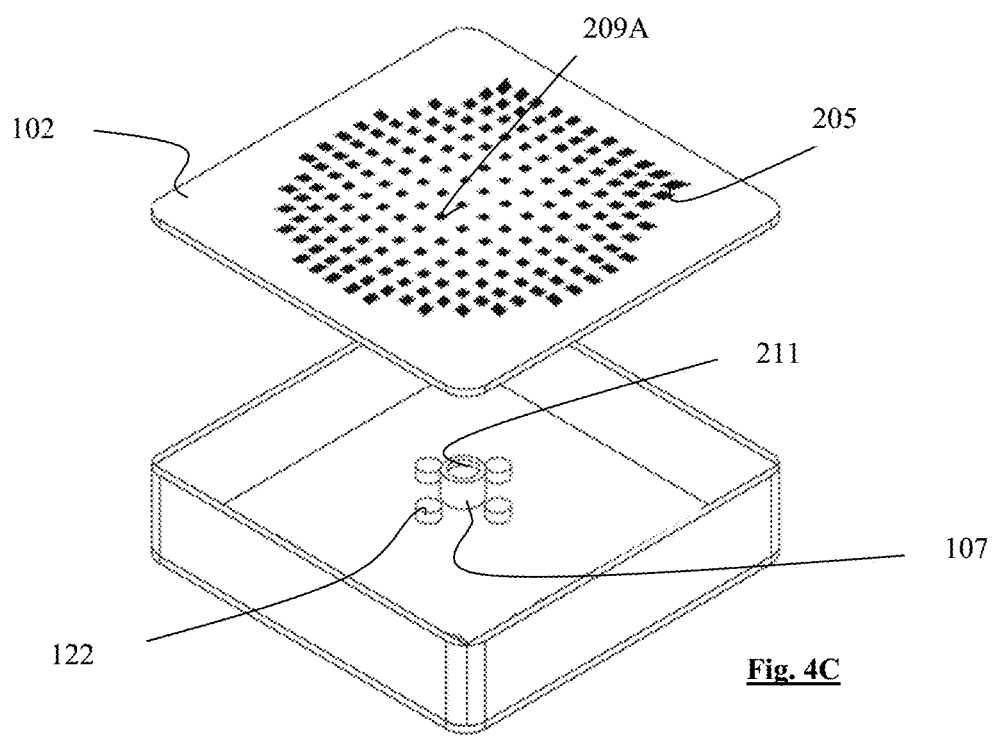

The warped shaped TLC formations 207A, 207B and the non-warped TLC formations 209A, 209B define a pattern such that when viewed through the wide angle lens 211 both the warped shaped TLC formations and the non-warped TLC formations appear non-warped as best illustrated in FIG. 4B. FIG. 4C illustrates a perspective view of the device 200 with the pattern of TLC formations 205 as illustrated in FIG. 4A provided on the transparent panel 102. It will be appreciated by those skilled in the art that while FIG. 4A illustrates a single image capture device 107 additional image capture devices may be provided as desired.

FIG. 4A illustrates an exemplary array of rhombus shaped TLC formations 205 which are designed such that the size, shape, and angle of the of the TLC results in a consistent square shape when observed through a wide angle lens 211 as illustrated in FIG. 4B. In the pattern of FIG. 4A the size, shape, and/or angle vary based on position relative to centre of image. The image of the pattern of FIG. 4A as viewed through the wide angle lens 211 is illustrated in FIG. 4B which illustrates that the TLC formations 205 have a consistent size, shape, and angle irrespective of their position relative to centre of image 215. FIG. 5A illustrates an exemplary array of elliptical-shaped TLC formations 205 which are designed such that the size, shape, and angle of the of the TLC results in a consistent circular shape when observed through the wide angle lens 211 as illustrated in FIG. 4B. In the pattern of FIG. 5A the size, shape, and/or angle vary based on position relative to centre of image. The image of the pattern of FIG. 4A as viewed through the wide angle lens 211 is illustrated in Figure which illustrates that the TLC formations 205 have a consistent size, shape, and angle irrespective of their position relative to centre of image 215. FIG. 5C illustrates a perspective view of the device 200 with the pattern of TLC formations 205 as illustrated in FIG. 5A provided on the transparent panel 102. It will be appreciated by those skilled in the art that while FIG. 5A illustrates a single image capture device 107 additional image capture devices may be provided as desired.

It will be appreciated by those skilled in the art that the term "warped shaped" have irregular geometry while the term non-warped shape have a regular geometry. The irregularity of the TLC formation geometry will have an angular component that is determined by the position of the TLC formation relative to the centre of the image, such that the majority of the formation distortion is in a radial direction.

In the exemplary arrangement, the amount of warping of the warped shaped TLC formations increases towards the periphery of the pattern. The shape of the TLC formations vary in size relative to a centre of the pattern such that the TLC formations towards the periphery of the pattern are larger than the TLC formations adjacent the centre of the pattern. The warp angle of the warped TLC formations vary such that the TLC formations towards the periphery of the pattern have a larger warp angle than the TLC formations adjacent the centre of the pattern. The captured image of the TLC formations have uniform dimensions irrespective of their position in the pattern. The captured image of the TLC formations have a uniform shape irrespective of their position in the pattern. The captured image of the TLC formations have a uniform angle irrespective of their position in the pattern. The captured image of the TLC formations have uniform dimensions irrespective of their position in the pattern.

The geometry of the TLC formations 205 may be tuned to the parameters of a particular wide angle lens 211, for example, the parameters may include at least one of focal length and field of view. The geometry of the TLC formations 205 may be tuned to the parameters of a particular image sensor (image capture device 122), for example, the parameters of the image sensor may include at least one of resolution and aspect ratio. In one example, the TLC formations 205 extend radially from a centre point 213 in the pattern and the level of warping of the TLC formations increases the further the TLC formation 200 is located from the centre point 213. The warp angle of the warped TLC formations 205 increases the further the TLC formations 205 is located from the centre point 213. The size of the warped TLC formations 205 increases the further the TLC formations 205 is located from the centre point 213. It will be appreciated by those skilled in the art that the 'warped shape' is a transformation of the 'reference shape' located at the centre point 213 in the pattern. For example, the 'reference shape' in FIG. 4A is a square which is transformed (warped) to a rhombus at locations extending radially from the centre point. In another example, the 'reference shape' in FIG. 5A is a circle which is transformed (warped) to a ellipse. The 'reference shape' may be bent or twisted out of shape and its dimensions may be varied in order to generate the 'warped shape'. In other words, the 'warped shape' may be a distorted version of the 'reference shape'.

The use of wide angle lenses has many advantage. It is advantageous to minimise the height of such the device 200, to make it as simple to use as possible, while simultaneously ensuring a sufficiently wide field of view is maintained to image the full with of the sole of the foot and the array of temperature sensors. This can be achieved through the use of wide angle lenses. Furthermore, wide angle lenses enable a wider field of view by compressing regions at the edge of the field of view, such that these regions light from these regions falls on the image sensor, where otherwise it would not with a lower field of view lens. The level of optical compression applied by the lens increased with distance from the centre of the lens.

Figure 2A:
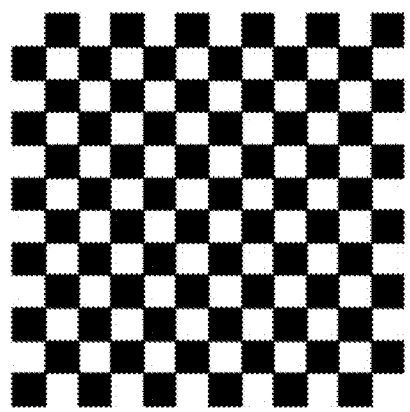
FIGS. 2A and 2B illustrates distortion as result of a wide angle lens.
Figure 2B:
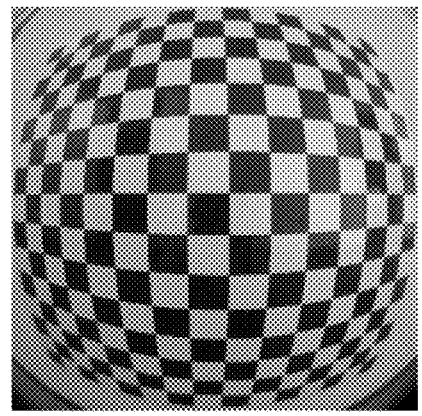
Figure 3:
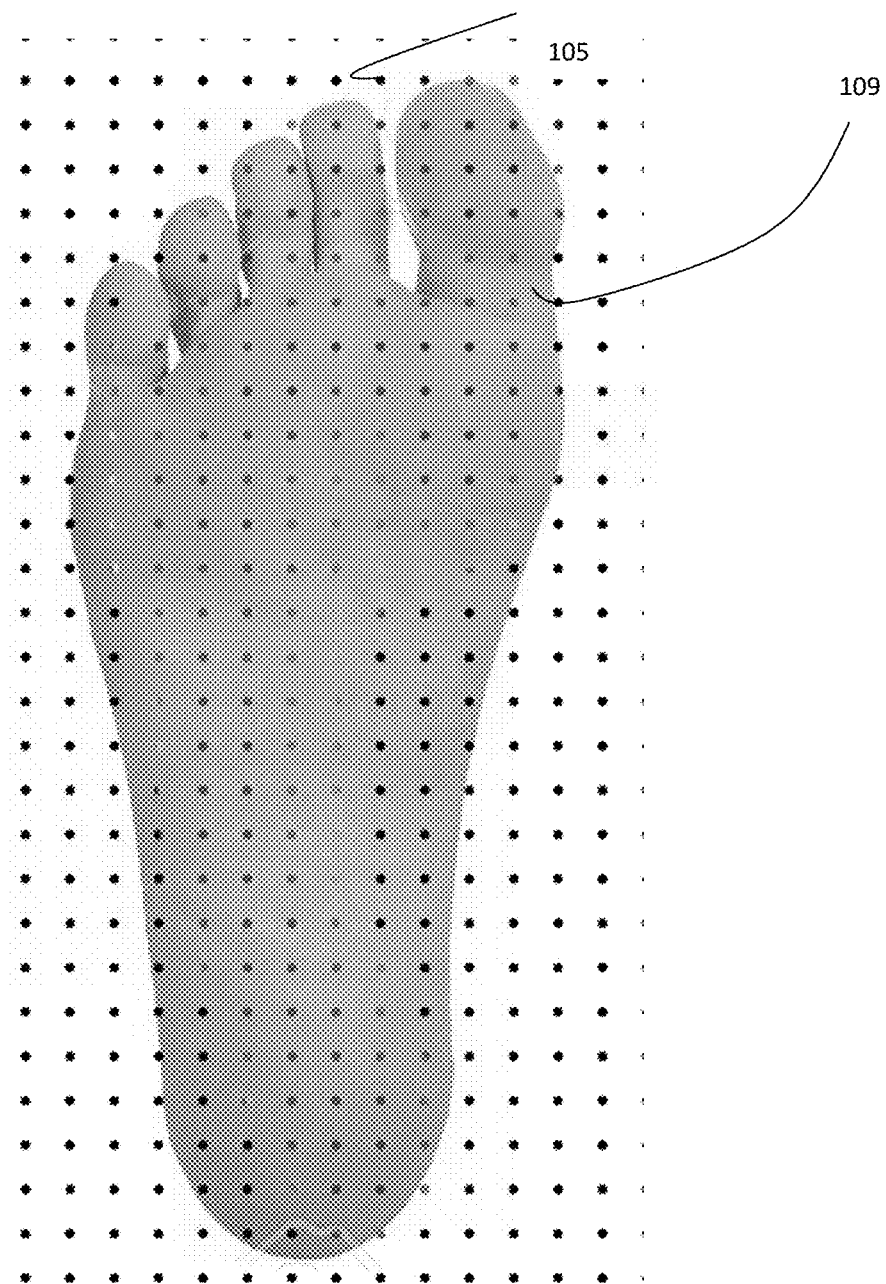
FIG. 3 illustrates a detail of an exemplary skin inspection device.

One of the drawbacks of wide angle lenses is the resulting distortion of the image, and the resulting change in the geometry of objects in the image. By way of example, a rectilinear checker board as illustrated in FIG. 2A when viewed through a wide angle lens will be distorted as shown in FIG. 2B, where the level of distortion and reduction in size of each square increases with distance from the centre of the image.

Image sensors are used to create a digital images by recording the level of light being transmitted towards the image sensor, typically for visible light within the portion of the electromagnetic spectrum that is perceived by the human eye, 400-700 nanometres (nm). Some image sensors may also record wavelengths above and below the visible light spectrum. Image sensors come in various different sizes such as ¼", ⅓", and ½. Image sensor come in a range of different resolutions typically give in megapixels (MP), such as 1MP, 5MP, 108MP etc. Resolution is calculated by multiplying the width and height of a sensor in pixels. So, a 2592×1944 image sensor that is has a total of 5,038,848 pixels, and if referred to as a 5MP image sensor.

As image sensors record light, it is required that the scene to be imaged has sufficient illumination to allow light transmission to the image sensor to record the information. Various different light sources may be used including sunlight, incandescent light bulbs, light emitting diodes (LEDs). Light is focused onto the image sensor using a lens. Fisheye lenses are a form of ultra-wide angle lenses that enable a wider field of view by compressing regions at the edge of the field of view, such that these regions light from these regions falls on the image sensor, where otherwise it would not with a lower field of view lens. Wide angle lenses typically have a field of view (FOV) in the range of 60° to 180° and in some cases up to well over 200°. The focal length of wide angle lenses can vary significantly such as under 4 mm and exceeding 30 mm. In addition some lenses have adjustable apertures, which may vary and is usually specified as an f-number, the ratio of focal length to effective aperture diameter, with typical ranges being from f/2.8-f/22. The level of optical compression applied by the lens increased with distance from the centre of the lens. One of the drawbacks of wide angle lenses is the resulting distortion of the image, and objects in the image. The distortion is related to the various lens parameters mentioned, and also due to the position of the object relative to the optical centre of the image, where typically the level of distortion increases with distance from the centre.

The impact of wide angle fisheye lens on thermochromic liquid crystal observations Region of Interest (ROI) will be appreciated by those skilled in the art. To measure temperature, colour information is measured from the area of the image where the TLC appears. The location of an ROI may be defined in pixel coordinates in the captured image. The centre pixel coordinate of an ROI is defined, along with the geometry of a boundary region centred on that pixel. For example, square boundaries may be defined by the height and width of the square in pixels e.g. 1×1, 3×3, 5×5 etc. The larger the region the number of pixels in the boundary, the more robust the colour signal is. For example, a 5×5 square ROI contains 25 pixels, where a 1×1 only contains 1. Hence it is advantageous that the TLC region in the captured image is of a size that that ensures that a minimum ROI may fit on the TLC.

FIG. 2 demonstrates how an object is compressed when viewed through a wide angle lens, and how this increases with distance from the centre. This means that TLC sensors of a consistent physical size will varying sizes in the captured image. Hence it would be advantageous to provide a means of ensuring that all TLC sensors have the same size in the in the image. Due to the nature of wide angle lenses, where the level of compression changes with distance from the centre of the image, this therefore means that the physical size of a TLC sensor required to meet the minimum ROI will vary based on position. However, it is also advantageous to minimise the size of the TLC sensors, to maximise the visibility of the foot behind then. Hence it is possible to design a sensor array that both meets the minimum TLC size threshold, while simultaneously minimising the size of the TLC sensors.

Two example array designs are given, based on two of the most common shapes used to define an area in image processing: squares as illustrated in FIG. 4A and circles as illustrated in FIG. 4B. However, this design methodology may be applied to any other shape as deemed appropriate and it will therefore be appreciated that it is not intended to limited the disclosure to the exemplary shapes described. The physical shape of the sensor will be designed/tuned to suit a particular lens specification (e.g. focal length, angle of view).

The use of wide angle lenses minimise the height of the device giving improved usability characteristics. The use of TLC sensors allows transparent optical pathways between sensors thus enabling simultaneous visual inspection. Minimising the size of the TLC sensors is therefore advantageous to maximise the visibility of the foot. In addition it reduces the amount of TLC material used and hence reduces cost. Noise in TLC sensors measurement increases as the size of the TLC ROI in the image decreases. Thus it is advantageous to ensure all TLC ROI's are above a certain threshold size, as this ensures sensor noise does rise to unacceptable levels. It is advantageous to maintain a consistent size of TLC ROI in captured image, so the level of noise is consistent across all sensors. Consistent ROI geometry in the captured image is advantageous for the application of image processing software to measure from the ROIs. No modification of the software sampling parameters is required for different regions, as all ROIs are the same geometry. This is advantageous for reducing the complexity of software and manufacturing processes.

Figure 6:
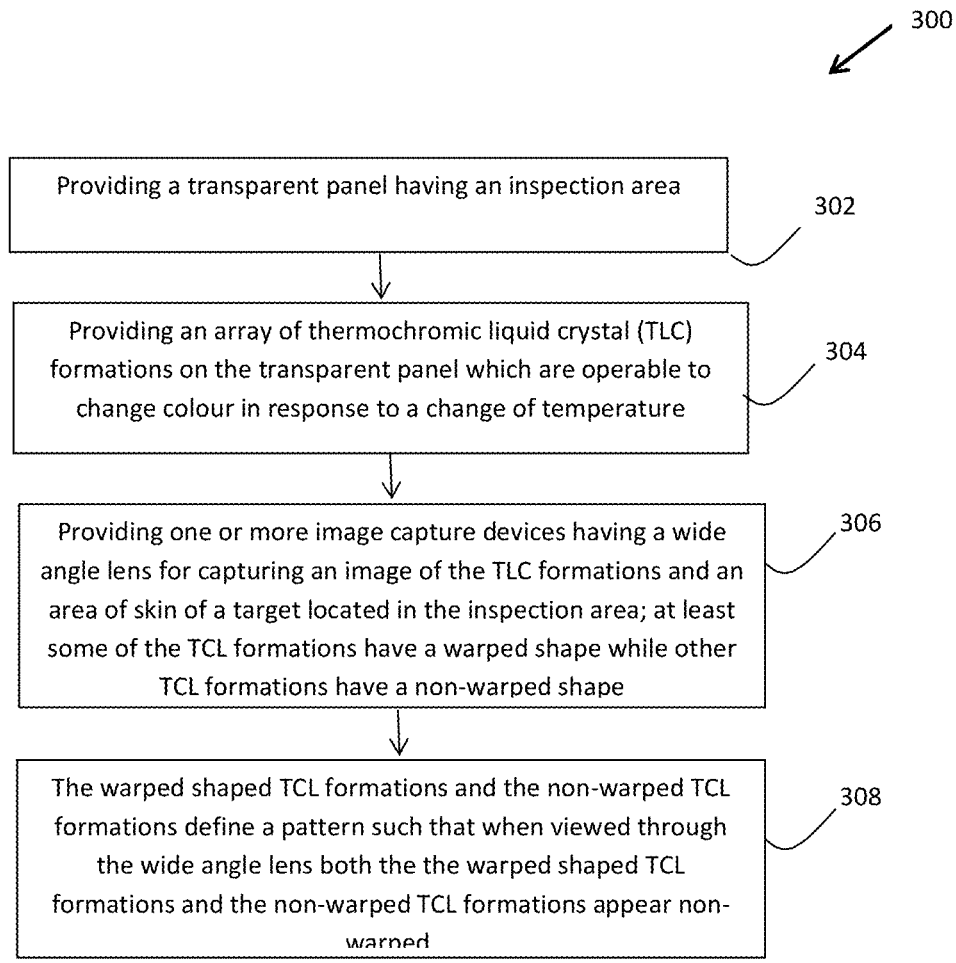
FIG. 6 is a flow chart detailing exemplary steps of a method for identifying skin abnormalities.

Referring to FIG. 6 which illustrates a flow chart 300 which details exemplary steps for identifying skin abnormalities. A transparent panel is provided having an inspection area; step 302. An array of thermochromic liquid crystal (TLC) formations on the transparent panel are provided which are operable to change colour in response to a change of temperature; step 304. One or more image capture devices are provided having a wide angle lens for capturing an image of the TLC formations and an area of skin of a target located in the inspection area; at least some of the TLC formations have a warped shape while other TLC formations have a non-warped shape; step 306. The warped shaped TLC formations and the non-warped TLC formations define a pattern such that when viewed through the wide angle lens both the warped shaped TLC formations and the non-warped TLC formations appear non-warped, step 308.

Figure 7A:
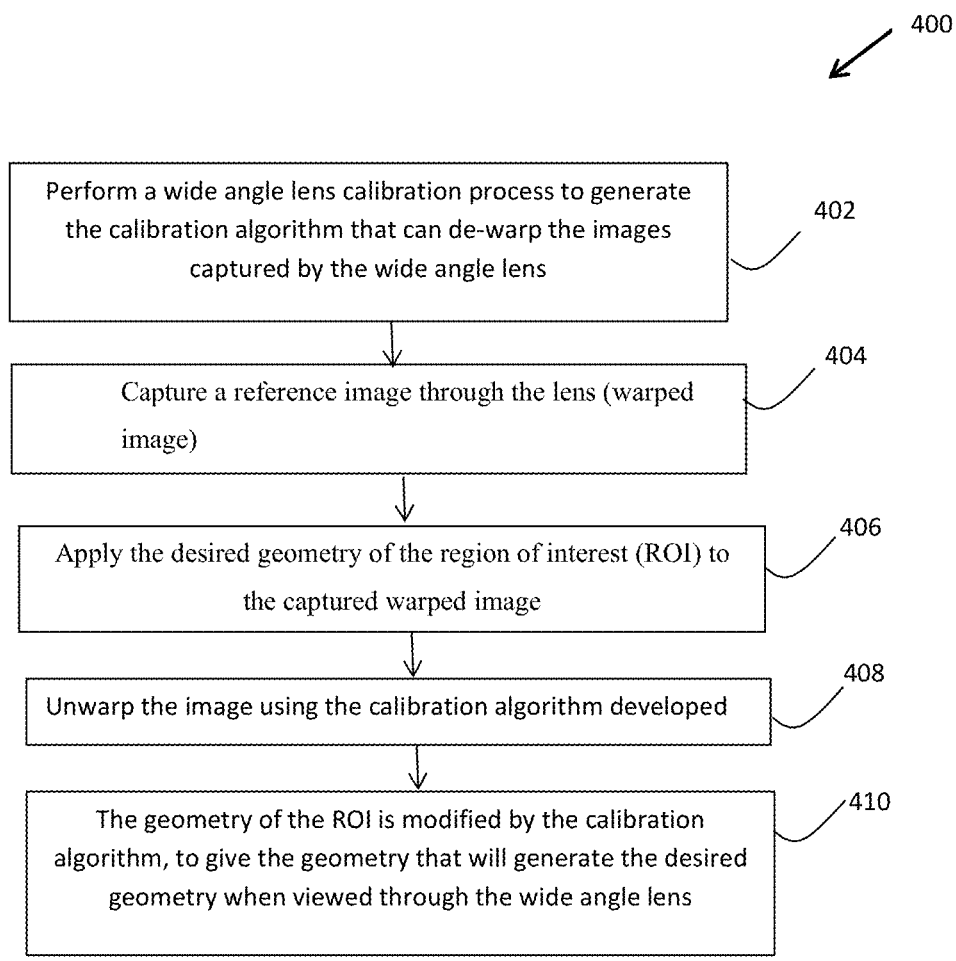
FIG. 7A is a flow chart detailing an exemplary approach to generating the physical geometry of a TLC sensor that will appear as a desired geometry when observed through a wide angle lens.

Referring to FIG. 7A which illustrates a flow chart 400 detailing an exemplary approach to generating the physical geometry of a TLC sensor that will appear as a desired geometry when observed through a wide angle lens. Step 402, perform wide angle lens calibration process to generate the calibration algorithm that can de-warp the images captured by the wide angle lens. Step 404, capture a reference image through the lens (warped image). Step 406, apply the desired geometry of the region of interest (ROI) to the captured warped image. Step 408, unwarp the image using the calibration algorithm developed. Step 410, the geometry of the ROI is modified by the calibration algorithm, to give the geometry that will generate the desired geometry when viewed through the wide angle lens.

Figure 7B:
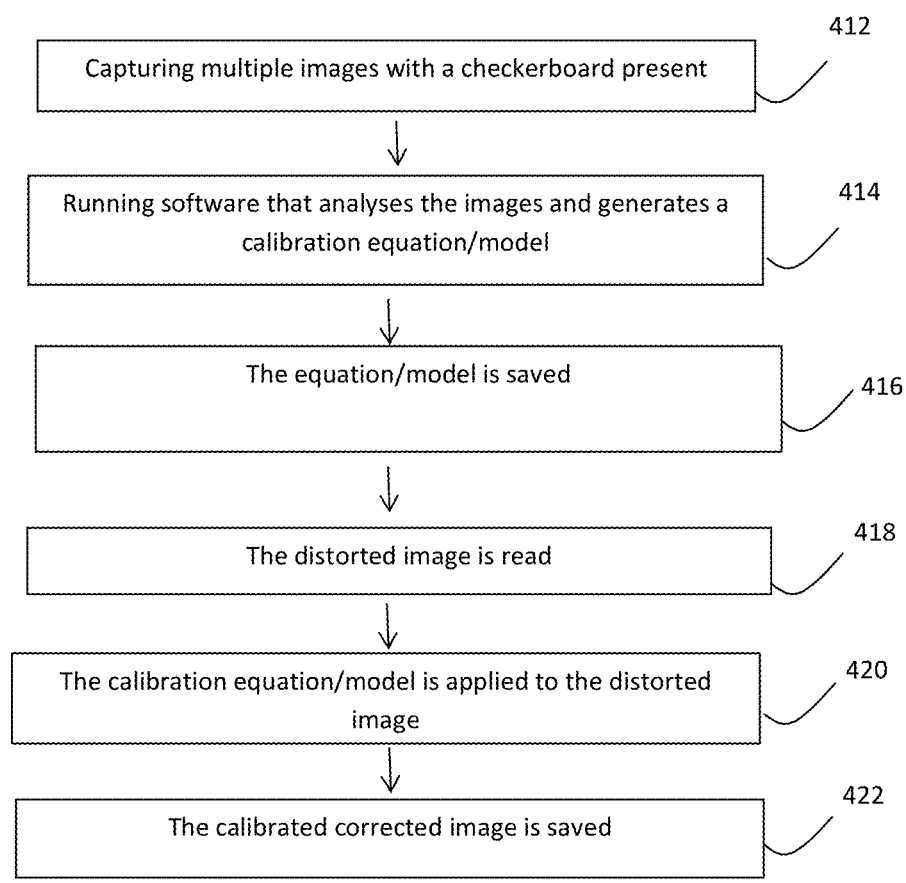
FIG. 7B is a flow chart detailing an exemplary calibration step.
Figure 8:
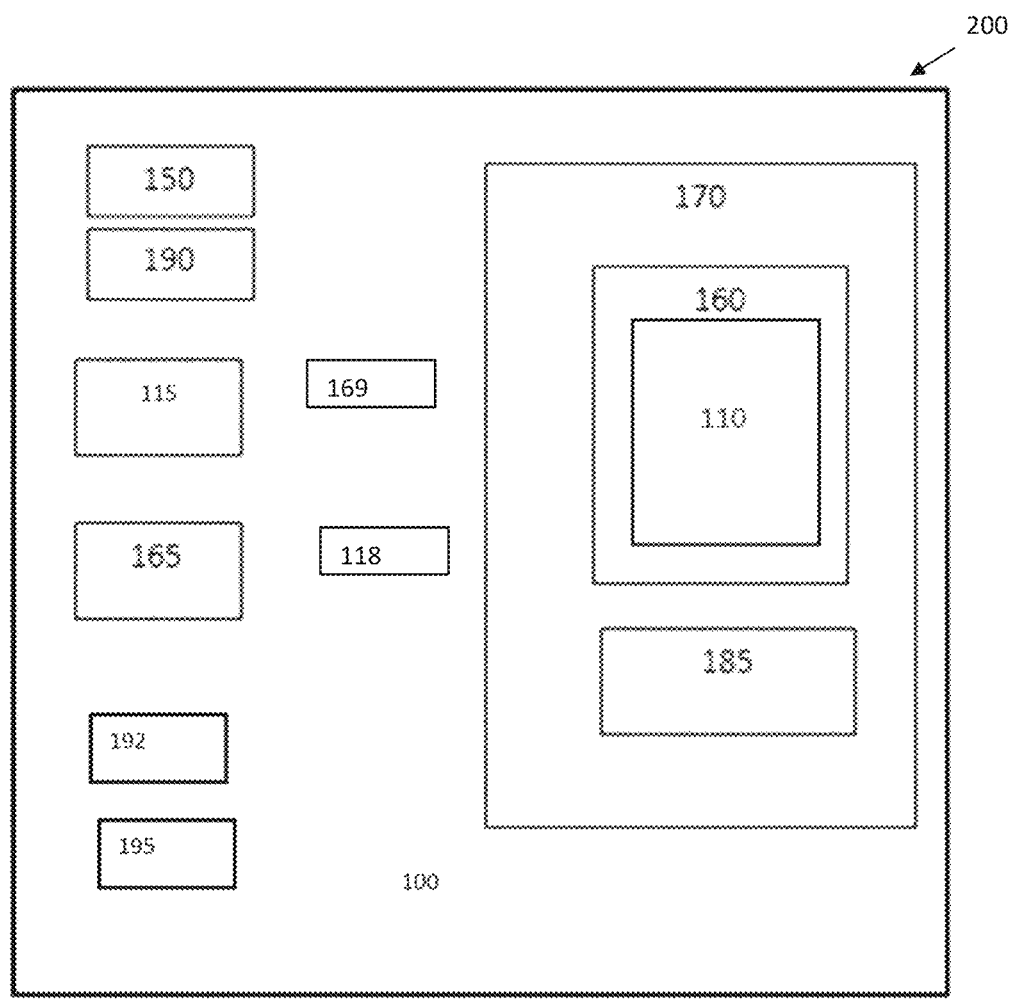
FIG. 8 illustrates exemplary components of a skin inspection device in accordance with the present teaching.
Figure 9:
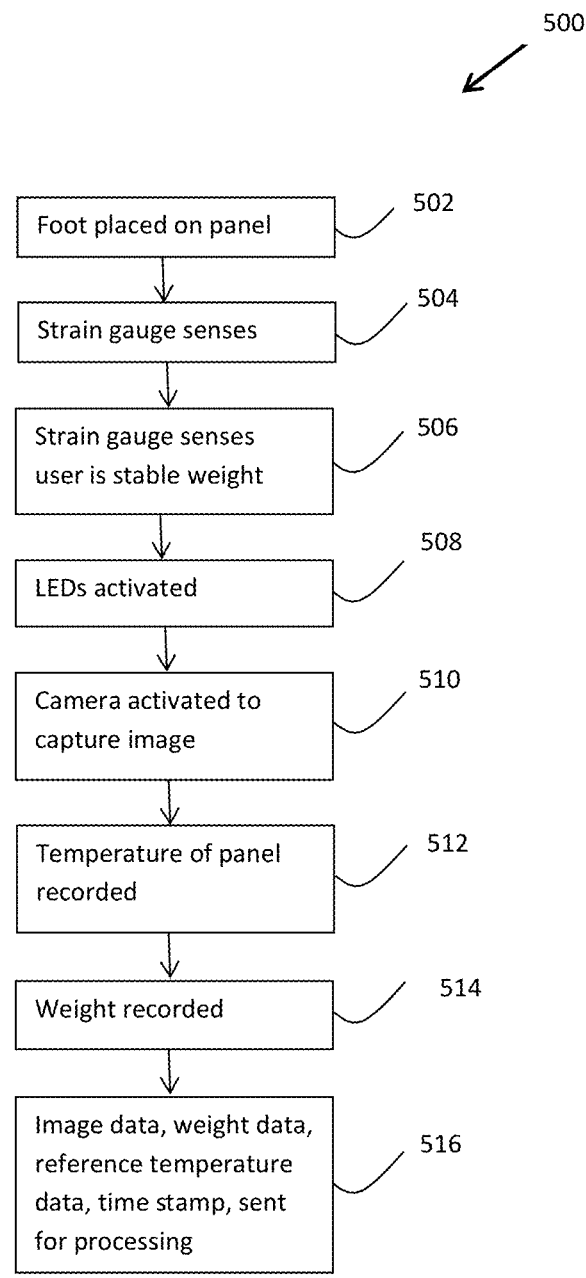
FIG. 9 is a flow chart detailing exemplary steps carried by a skin inspection device in accordance with the present teaching.

Wide angle lens calibration will be understood by those skilled in the art as a means of generating a mapping function that will convert the warped image captured by the wide angle lens to an unwarped rectilinear. The method described by Scaramuzza et al (A Toolbox for Easily Calibrating Omnidirectional Cameras 2006) is widely known. Step 402 is expanded by exemplary steps as illustrated in FIG. 7B. It involves a process of capturing multiple images with a checkerboard present step 412 and then running software that analyses the images and generates a calibration equation/model, step 414. The equation/model is saved, step 416, and may be applied in the unwarping step of 408. The calibration takes into account lens parameters such as focal length, field of view. The distorted image is read, step 418. The calibration equation/model is applied to the distorted image, step 420. The calibrated corrected image is saved, step 422.

Thus by using the method described in this disclosure, it is understood that this approach can be taken to determine the physical shape of an object required to achieve a desired observed shape, and will work for any combination of image sensor, lens, light source, and desired TLC formation shape.

It will be appreciated that the device 200 includes one or more software modules which are programmed to implement predefined functions. The device 200 includes various hardware and software components that function to perform the methods according to the present disclosure. The device 200 comprises a user interface 150, CPU 115 in communication with a memory 160, and a communication interface 165. The CPU 115 functions to execute software instructions that can be loaded and stored in the memory 160. The CPU 115 may include a number of processors, a multi-processor core, or some other type of processor, depending on the particular implementation. The memory 160 may be accessible by the CPU 115, thereby enabling the CPU 115 to receive and execute instructions stored on the memory 160. The memory 160 may be, for example, a random access memory (RAM) or any other suitable volatile or non-volatile computer readable storage medium. In addition, the memory 160 may be fixed or removable and may contain one or more components or devices such as a hard drive, a flash memory, a rewritable optical disk, a rewritable magnetic tape, or some combination of the above.

One or more software modules 170 may be encoded in the memory 160. The software modules 170 may comprise one or more software programs or applications having computer program code or a set of instructions configured to be executed by the processor 115. Such computer program code or instructions for carrying out operations for aspects of the systems and methods disclosed herein may be written in any combination of one or more programming languages. During execution of the software modules 170, the CPU 115 configures the device 200 to perform various operations relating to identifying the formation of skin abnormalities according to embodiments of the present disclosure. The CPU 115 may be configured to process the image captured by the image capture device 107 for determining the temperature of the target at multiple discrete locations. The CPU 115 may be operable to process the image and convert the colours of the identified TLC formations into corresponding temperature values. The CPU 115 may be programmed to convert the colours of the identified TLC formations into corresponding temperature values based on a hue/saturation/lightness of the dot and a colour-temperature conversion table. It will be appreciated by those skilled in the art that other colour spaces such as hue/saturation/value (HSV) or red, green, blue (RGB) may be used. Additionally, the CPU 115 may be configured to generate a temperature map based on the temperature values. In one exemplary arrangement, the CPU 115 is operable to overlay the temperature map onto the captured image of the target. In another arrangement, the CPU 115 is configured to perform image analysis on the temperature map and the captured image. The CPU may be programmed to compare the temperature at similar points of the captured image. The CPU 115 may be operable to generate indicia indicative of the emergence of ulcers and/or other skin abnormalities based on image analysis of the captured image. The CPU 115 may be operable to generate indicia indicative of the emergence of ulcers and/or other skin abnormalities at particular locations on the captured image. The indicia may be in the form of an output image, for example. In another example, the CPU 115 is configured to detect for areas on the captured images including at least one of excess callous, blisters, moisture, and discolouration.

Other information and/or data relevant to the operation of the present systems and methods, such as a database 185, may also be stored on the memory 160. The database 185 may contain and/or maintain various data items and elements that are utilized throughout the various operations. It should be noted that although the database 185 is depicted as being configured locally to the device 100, in certain implementations the database 185 and/or various other data elements stored therein may be located remotely. Such elements may be located on a remote device or server—not shown, and connected to the device 100 through a network in a manner known to those skilled in the art, in order to be loaded into a processor and executed.

Further, the program code of the software modules 170 and one or more computer readable storage devices (such as the memory 160) form a computer program product that may be manufactured and/or distributed in accordance with the present disclosure, as is known to those of skill in the art.

The communication interface 165 is also operatively connected to the CPU 115 and may be any interface that enables communication between the device 100 and external devices, machines and/or elements. The communication interface 165 is configured for transmitting and/or receiving data. For example, the communication interface 165 may include but is not limited to a Bluetooth, WiFi; or cellular transceiver, a wireless module, a satellite communication transmitter/receiver, an optical port and/or any other such, interfaces for connecting the device 110 to external devices.

The user interface 150 is also operatively connected to the CPU 115. The user interface may comprise one or more input device(s) such as switch(es), button(s), key(s), or a touchscreen. The user interface 150 functions to allow the entry of data. The user interface 150 functions to facilitate the capture of commands from the user such as an on-off commands or settings related to operation of the above-described method.

A display 190 may also be operatively connected to the CPU 115. The display 190 may include a screen or any other such presentation device that enables the user to view various options, parameters, and results. The display 190 may be a digital display such as an LED display. The device 110 may be powered via a power supply 192. An alert mechanism 195 is provided for generating alerts. The alert mechanism 195 is operable to communicate the alert to a remote entity via a telecommunications network.

An exemplary operation of the device 200 is described with reference to the flowcharts 500, 300A, 300B and 300C. In block 502 a user steps onto the transparent panel 102. A strain gauge 169 which is operably coupled to the CPU 115 sense the weight load on the transparent panel 102, block 504. The strain gauge 169 is configured to determine when the user is in a stable position, block 506. The CPU 115 activates the LEDs 122, block 508. In this exemplary embodiment, two image capture device 107 are activated to capture an image of the sole of the individuals foot 109 as well as the pattern of the TLC dots 105 that have changed colour to indicate the temperature of the corresponding points on the sole of the foot 109, block 510. A temperature sensor 118 records the temperature of the transparent panel 102, block 512. In this example, the skin inspection device 110 may also function as a weighing scales to capture the individual's weigh, block 514. The image data, weight data, reference temperature data, time stamp are sent to the CPU 115 for processing, step 516.

Figure 10:
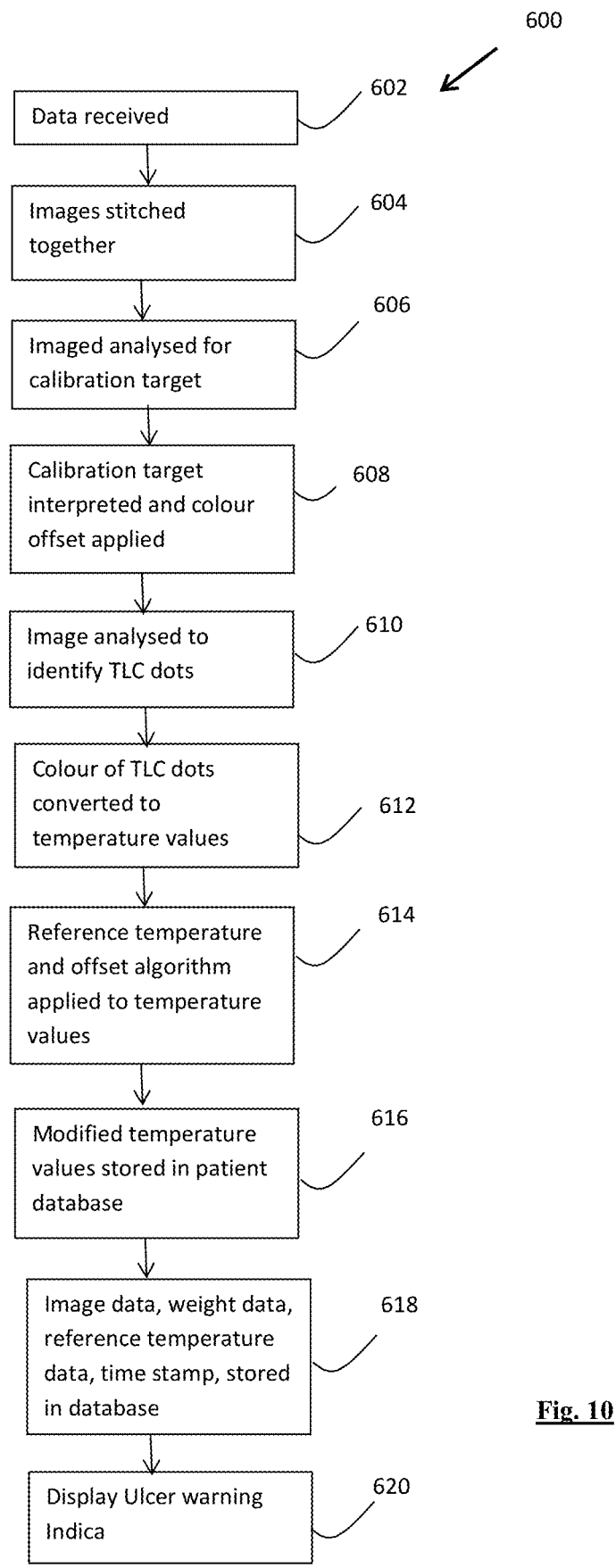
FIG. 10 is a flow chart detailing exemplary steps carried by a skin inspection device in accordance with the present teaching.

The data processing is described with reference to the flowchart 600 of FIG. 10. The CPU 115 receives the image data, weight data, reference temperature data, time stamp, block 602. Since two image capture devices were used to capture the image data, the captured images are stitched together, block 604. The CPU 115 analyses the captured image for a colour calibration target, block 606. The CPU 115 interprets the colour calibration target and applies a colour offset to the captured image, block 608. Furthermore, the locations of the TLC dots 105 are identified by the CPU 115, block 610. The colour of the TLC dots 105 are converted to temperature values by the CPU 115, block 612. The reference temperature and offset algorithm are applied to the temperatures values by the CPU 115, block 614. The modified temperatures values are stored in a patient database, block 616. The image data, weight data, reference temperature and time stamp are also stored in the database 618. If it is determined that the temperature values indicate the formation of DFU an appropriate indicia is displayed on the display 190 alerting the individual of a potential ulceration, block 620.

Figure 11:
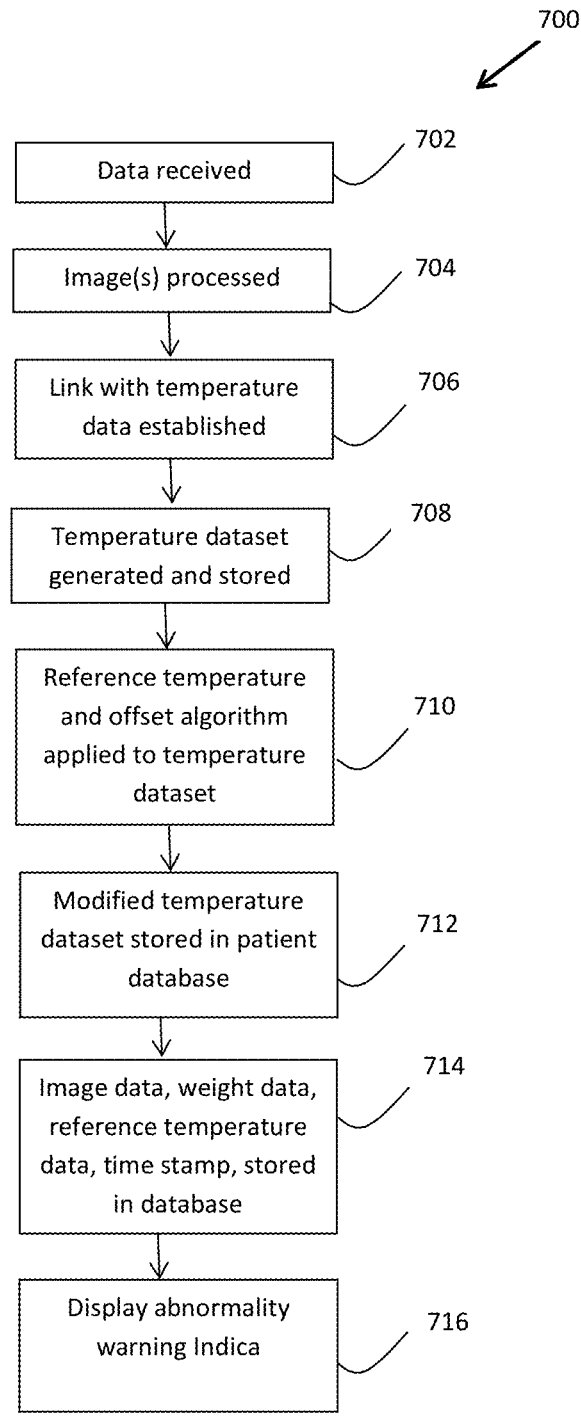
FIG. 11 is a flow chart detailing exemplary steps carried by a skin inspection device in accordance with the present teaching.

An exemplary data processing approach is described with reference to the flowchart 700 of FIG. 11. The CPU 115 receives the image data, weight data, reference temperature data, time stamp, block 702. The image data is processed by the CPU 115, block 704. This processing may include the CPU 115 applying an algorithm that would scan the captured image and identify the location of the temperature sensors 105. The locations of the temperature sensors 105 in the captured image are linked to temperature data recorded by the sensors 105, block 706. The CPU 115 generates a temperature dataset based on the recorded temperature values of the sensors 105, block 708. The temperature dataset is stored in database 185. The reference temperature and offset algorithm are applied to the temperature dataset by the CPU 115, block 710. The modified temperature dataset is stored in a patient database, block 712. The image data, weight data, reference temperature and time stamp are also stored in the database, block 714. If it is determined that the temperature values in the temperature dataset indicate the formation of DFU an appropriate indicia is displayed on the display 190 alerting the individual of a potential ulceration, block 716. It will be appreciated that it is not intended to limited the present teaching to the exemplary steps provided or to the order and sequence of the steps which may be modified as desired. For example, the inclusion of the weight data may be optional in the data processing approach described above.

The system may be configured to detect visual or thermal abnormalities, or a combination of both, block 318. Visual abnormalities may be detected by first identifying the feet within the image. The feet are then reviewed for abnormal features. Thermal abnormalities may be identified by using just the thermal data, or by combining the visual image with the thermal data. The location of the foot may be determined using the visual image. This is advantageous as there are occasions when the temperate of the feet is similar to ambient temperature, and hence it can be difficult to determine the location of the feet using thermal data alone. As such it can be difficult to perform comparisons between points on one foot and the other as it is difficult to determine which points to compare.

By linking the images of the feet with the temperature dataset it is possible to determine the temperature at any location on the foot. Abnormalities may be detected by comparing the temperature between like for like points on the feet (a contralateral comparison). Other methods of detecting abnormalities may include comparing the average, maximum, minimum temperature, or any other statistically generated number. Another method is to compare the data collected to previously collected data. In certain patients there may be a pre-existing temperature difference between contralateral sites, and in these instances it would be advantageous to compare the temperature to previously recorded temperatures. In another embodiment, a comparison of regional temperatures may be carried out, such as the forefoot, the heel, the hallux etc.

It is advantageous to review two different sensing modality datasets (thermal and visual) as it increases the level of information available to determine the presence of abnormalities. Some abnormalities may only be present in one of the datasets. It is advantageous as in gives four potential outcomes, whereas with a single sensing modality there are only two.

| Outcome | Thermal | Visual |
|---------|---------|--------|
| 1 | OK | OK |
| 2 | OK | Not OK |
| 3 | Not OK | OK |
| 4 | Not OK | Not OK |

The system may be configured to alter the alert based on the type of abnormalities detected. For example the indicia generated by a contralateral temperature increase without the presence of a visual abnormality may be different to the indicia generated if an active ulcer is detected.

Points in the image may be used to identify physical items such as toes, heel, arch, etc. The image may be digitised in order to generate a geometrical map of the foot. Different areas of the images may be classified based on characteristic. These classified areas may be used as reference point(s) when comparing both feet. The geometrical map may be used to identify a physical formation at a given coordinate. Thus the geometrical map allows accurate comparison to the same region on the other foot. This facilitates easy mapping data from each foot at similar points.

Foot temperate is usually below body temperature. Often foot temperature can be similar temperature to ambient temperature. In such instances, it is not possible to determine where in a heat map corresponds to the foot. Hence it can be difficult to perform a contralateral temperature comparison.

It will be appreciated by the person of skill in the art that various modifications may be made to the above described embodiments without departing from the scope of the present invention. In this way it will be understood that the teaching is to be limited only insofar as is deemed necessary in the light of the appended claims. For ease of description, the TLC formations have been referred to as dots through out this disclosure. However, a number of different shapes may be used, for example but not limited to, circular, triangular, square, oval, pentagon, stars, chevrons, lines, curves etc. It is envisaged that the TLC formations can be provided in any desired configuration. In the exemplary arrangement; multiple image capture devices are illustrated, however, it will be appreciated that a single image capture device may be used.

An advantage of using an array of TLC dot formations is that it enables acquisition of temperature data at a high number of discrete locations, while maintaining the ability to capture a visual image of the target location. For example, the following table presents the percentage of the image obscured by TLC dots of various diameter. In the example the dots are located at a pitch of 1 cm, whereby every 100 mm² contains a single dot. The area of a circle is give by:

$$\pi \cdot r^2$$

where r is the radius of the circle

| Dot Diameter | Dot Area | Panel Transparency |
|---|---|---|
| 2 mm | 3.14 mm² | 96.86% |
| 3 mm | 7.07 mm² | 92.93% |
| 4 mm | 12.57 mm² | 87.43% |

In this way, due the dispersed nature and the dimensions of the TLC dots they do not obscure a significant portion of the surface area of the sole of the foot from the view of the image capture device.

It will be appreciated by the person of skill in the art that various modifications may be made to the above described embodiments without departing from the scope of the present invention. In this way it will be understood that the teaching is to be limited only insofar as is deemed necessary in the light of the appended claims. In an exemplary embodiment; the skin inspection device 200 may be incorporated into a weighing scales which would have a means for calculating the weight of an individual.

Similarly the words comprises/comprising when used in the specification are used to specify the presence of stated formations, integers, steps or components but do not preclude the presence or addition of one or more additional formations, integers, steps, components or groups thereof.

The invention claimed is:

1. A skin inspection device for identifying abnormalities, the device comprising:
   a transparent panel having an inspection area;
   an array of thermochromic liquid crystal (TLC) formations provided on the transparent panel which are operable to change colour in response to a change of temperature; and
   one or more image capture devices having a wide angle lens for capturing an image of the array of TLC formations and an area of skin of a target located in the inspection area; the array of TLC formations comprises warped-shaped TLC formations and non-warped-shaped TLC formations;
   wherein the warped-shaped TLC formations and the non-warped TLC formations define a pattern, in which warping of the warped-shaped TLC formations increases towards the periphery of the pattern, such that when viewed through the wide angle lens both the warped-shaped TLC formations and the non-warped TLC formations appear non-warped.

2. The skin inspection device as claimed in claim 1, wherein the shape of the TLC formations vary in size relative to a centre of the pattern such that the TLC formations towards the periphery of the pattern are larger than the TLC formations adjacent the centre of the pattern.

3. The skin inspection device as claimed in claim 1, wherein a warp angle of the warped TLC formations varies such that the TLC formations towards the periphery of the pattern have a larger warp angle than the TLC formations adjacent the centre of the pattern.

4. The skin inspection device as claimed in claim 1, wherein the TLC formations of the captured image have uniform dimensions irrespective of their position in the pattern.

5. The skin inspection device as claimed in claim 1, wherein the TLC formations of the captured image have a uniform shape irrespective of their position in the pattern.

6. The skin inspection device as claimed in claim 1, wherein the TLC formations of the captured image have a uniform angle irrespective of their position in the pattern.

7. The skin inspection device as claimed in claim 1, wherein a geometry of the TLC formations are tuned to one or more parameters of a particular wide angle lens, wherein the one or more parameters of the wide angle lens include focal length or field of view.

8. The skin inspection device as claimed in claim 1, wherein a geometry of the TLC formations are tuned to one or more parameters of a particular image sensor, wherein the one or more parameters of the particular image sensor include resolution or aspect ratio.

9. The skin inspection device as claimed in claim 1, wherein the TLC formations extend radially from a centre point in the pattern and warping of the TLC formations increases the further the TLC formation is located from the centre point.

10. The skin inspection device as claimed in claim 9, wherein a warp angle of the warped TLC formations increases the further the TLC formations is located from the centre point.

11. The skin inspection device as claimed in claim 9, wherein a size of the warped TLC formations increases the further the TLC formations is located from the centre point.

12. A method for identifying skin abnormalities; the method comprising:
   providing a transparent panel having an inspection area;
   providing an array of thermochromic liquid crystal (TLC) formations on the transparent panel which are operable to change colour in response to a change of temperature; and
   providing one or more image capture devices having a wide angle lens for capturing an image of the array of TLC formations and an area of skin of a target located in the inspection area; the array of TLC formations comprises warped-shaped TLC formations and non-warped-shaped TLC formations;
   wherein the warped-shaped TLC formations and the non-warped TLC formations define a pattern, in which warping of the warped-shaped TLC formations increases towards the periphery of the pattern, such that when viewed through the wide angle lens both the warped-shaped TLC formations and the non-warped TLC formations appear non-warped.

13. The method as claimed in claim 12, wherein the shape of the TLC formations vary in size relative to a centre of the pattern such that the TLC formations towards the periphery of the pattern are larger than the TLC formations adjacent the centre of the pattern.

14. The method as claimed in claim 12, wherein a warp angle of the warped TLC formations varies such that the TLC formations towards the periphery of the pattern have a larger warp angle than the TLC formations adjacent the centre of the pattern.

15. The method as claimed in claim 12, wherein the TLC formations of the captured image have uniform dimensions irrespective of their position in the pattern.

16. The method as claimed in claim 12, wherein the TLC formations of the captured image have a uniform shape irrespective of their position in the pattern.

17. The method as claimed in claim 12, wherein the TLC formations of the captured image have a uniform angle irrespective of their position in the pattern.

18. The method as claimed in claim 12, wherein a geometry of the TLC formations are tuned to one or more parameters of a particular wide angle lens, wherein the one or more parameters include focal length and field of view.

19. The method as claimed in claim 12, wherein a geometry of the TLC formations are tuned to one or more parameters of a particular image sensor, wherein the one or more parameters include resolution and aspect ratio.

20. The method as claimed in claim 12, wherein the TLC formations extend radially from a centre point in the pattern and warping of the TLC formations increases the further the TLC formation is located from the centre point.

21. The method as claimed in claim 20, wherein a warp angle of the warped TLC formations increases the further the TLC formations is located from the centre point.

22. The method as claimed in claim 20, wherein a size of the warped TLC formations increases the further the TLC formations is located from the centre point.

* * * * *